United States Patent

Massoni

(10) Patent No.: US 7,578,857 B1
(45) Date of Patent: Aug. 25, 2009

(54) COLOR SHAMPOO FORMULA

(75) Inventor: Jack Massoni, New Fairfield, CT (US)

(73) Assignee: Combe Incorporated, White Plains, NY (US)

( * ) Notice: Subject to any disclaimer, the term of this patent is extended or adjusted under 35 U.S.C. 154(b) by 0 days.

(21) Appl. No.: 12/317,503

(22) Filed: Dec. 24, 2008

(51) Int. Cl.
*A61Q 5/10* (2006.01)

(52) U.S. Cl. .................. 8/405; 8/426; 8/435; 8/525; 8/654; 8/586; 132/202; 132/208; 510/123; 510/124; 510/126

(58) Field of Classification Search ............ 8/405, 8/426, 435, 525, 654, 586; 132/202, 208; 510/123, 124, 126
See application file for complete search history.

(56) References Cited

U.S. PATENT DOCUMENTS

| | | | |
|---|---|---|---|
| 5,145,482 A | 9/1992 | Clausen | |
| 5,221,530 A * | 6/1993 | Janchitraponvej et al. | 424/70.11 |
| 5,468,256 A | 11/1995 | Braun | |
| 6,200,554 B1 | 3/2001 | Yeoh | |
| 6,432,146 B1 | 8/2002 | Rondeau | |
| 6,540,791 B1 | 4/2003 | Dias | |
| 6,605,577 B1 | 8/2003 | Harrison | |
| 6,835,018 B2 | 12/2004 | Miczewski | |
| 7,094,262 B2 | 8/2006 | Lagrange | |
| 7,105,032 B2 | 9/2006 | Gross | |
| 7,135,168 B2 | 11/2006 | Miczewski | |
| 7,217,752 B2 | 5/2007 | Schmucker | |
| 2003/0143177 A1 | 7/2003 | Stella | |
| 2003/0159221 A1 | 8/2003 | Lang | |
| 2004/0087668 A1 | 5/2004 | Schmucker | |
| 2004/0221399 A1 | 11/2004 | Cotteret | |
| 2004/0237213 A1 | 12/2004 | Plos | |
| 2005/0005370 A1 | 1/2005 | Lim | |
| 2005/0039272 A1 | 2/2005 | Miczewski | |
| 2007/0017039 A1 | 1/2007 | Errey | |
| 2007/0044251 A1 | 3/2007 | Kravtchenko | |
| 2007/0067924 A1 | 3/2007 | Beck | |

FOREIGN PATENT DOCUMENTS

EP 1 504 749 A1 2/2005
WO WO2006/118942 A2 11/2006

* cited by examiner

*Primary Examiner*—Eisa B Elhilo
(74) *Attorney, Agent, or Firm*—James V. Costigan; Hedman & Costigan, P.C.

(57) ABSTRACT

A shampoo coloring formulation for human hair having the following ingredients;
(a) cationic dye;
(b) sodium lauroyl sarcosinate;
(c) lauramidopropyl betaine;
(d) cocamido propylamine oxide;
(e) lauramide MEA and
(f) water.

12 Claims, 2 Drawing Sheets

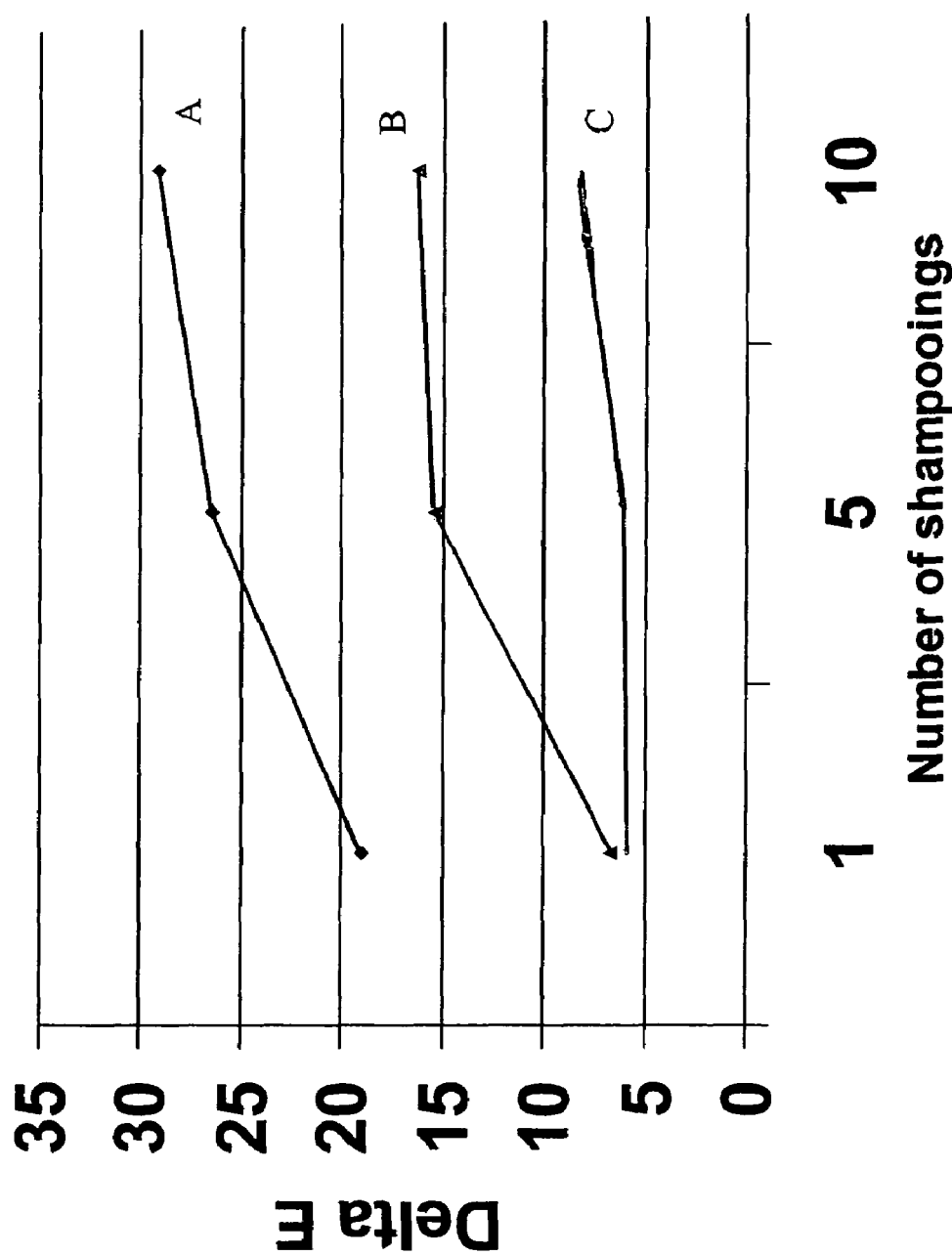

COLOR SHAMPOO FORMULA

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

REFERENCE TO A MICROFICHE APPENDIX

Not Applicable

BACKGROUND OF THE INVENTION

1) Field of the Invention

The present invention is concerned with the application of a dye to human hair using a one-part shampoo based formulation.

2) Description of Related Art

Certain hair dyes, namely Basic Blue 99, Basic Brown 16, Basic Brown 17, Basic Red 76, and Basic Yellow 57 have been available for use in cosmetic products since the 1970's. They were specifically designed to be used as hair colorants, and have been adapted for use in color refreshing shampoos and conditioners since their commercial availability. These products were intended to enhance previously colored hair by attaching themselves to anionic sites on the hair's surface. The dyes listed above have cationic charges on the dye molecule and are well suited for instant coloration in this fashion. They have only been used as refreshing products as the damage caused by oxidation haircoloring compositions increased the anionic sites to a degree where a small deposit of coloration can occur each time the hair is shampooed. This would then maintain a fresh colored appearance of the hair that had been treated with an oxidation haircolor. Any new re-growth of pigmented or gray hair would not be affected by the refreshing shampoo which required an additional retouch of oxidation haircolor every four to six weeks. The present invention is concerned with the coloring of gray hair that has not been subjected to a prior oxidation haircoloring process or to other chemical treatments that would increase the anionic sites on the hair's surface. It will deposit increasing amounts of color when used daily over a two to three week period. At that point the number of anionic sites are depleted and the degree of coloration will plateau. A particular advantage of the shampoo formulation of the invention is that there is no need for an additional treatment to help reduce the amount of visible gray hair. The shampoo can replace one's normal product that is used to clean head hair and will color gray hair.

SUMMARY OF THE INVENTION

The present invention is directed to a shampoo based coloring composition comprising:
(a) a cationic dye;
(b) sodium lauroyl sarcosinate;
(c) lauramidopropyl betaine;
(d) cocamido propylamine oxide;
(e) lauramide MEA; and
(f) water.

A preferred shampoo dye formulation will comprise:
(a) from 0.5-2 wt % a cationic dye;
(b) from 5-15 wt % sodium lauroyl sarcosinate;
(c) from 5-15 wt % lauramidopropyl betaine;
(d) from 2.5-10 wt % cocamidopropylamine oxide;
(f) from 2.5-10 wt % lauramide MEA; and
(e) from 40-65 wt % water.

The above described compositions are described using the term "comprising" and "comprises" to point out compositions that are open to the inclusion of other ingredients that that may alter the characteristics of the formula without rendering them inoperative as shampoo dyes. The invention also includes the above listed ingredients in a composition which "consists essentially of" these ingredients where the composition excludes other active ingredients but may include stabilizer, fragrances, thickeners, chelating agents, opacifier's buffering agents and other adjuvants.

It is a primary object of the invention to provide a shampoo based formulation that will color gray or white hair without the need to use an oxidative dye.

It is also an object of the invention to provide a shampoo based formulation that will replace an ordinary shampoo but will be useful as a hair dye for gray and white hair.

BRIEF DESCRIPTION OF THE DRAWINGS

FIG. 2 is a graph of the results of a comparative test of the formulation of Example 1 of the present invention with a formulation of U.S. Pat. No. 7,217,775B2 and U.S. 2007/0017039 on white hair.

DETAILED DESCRIPTION OF THE INVENTION

Figure 1:
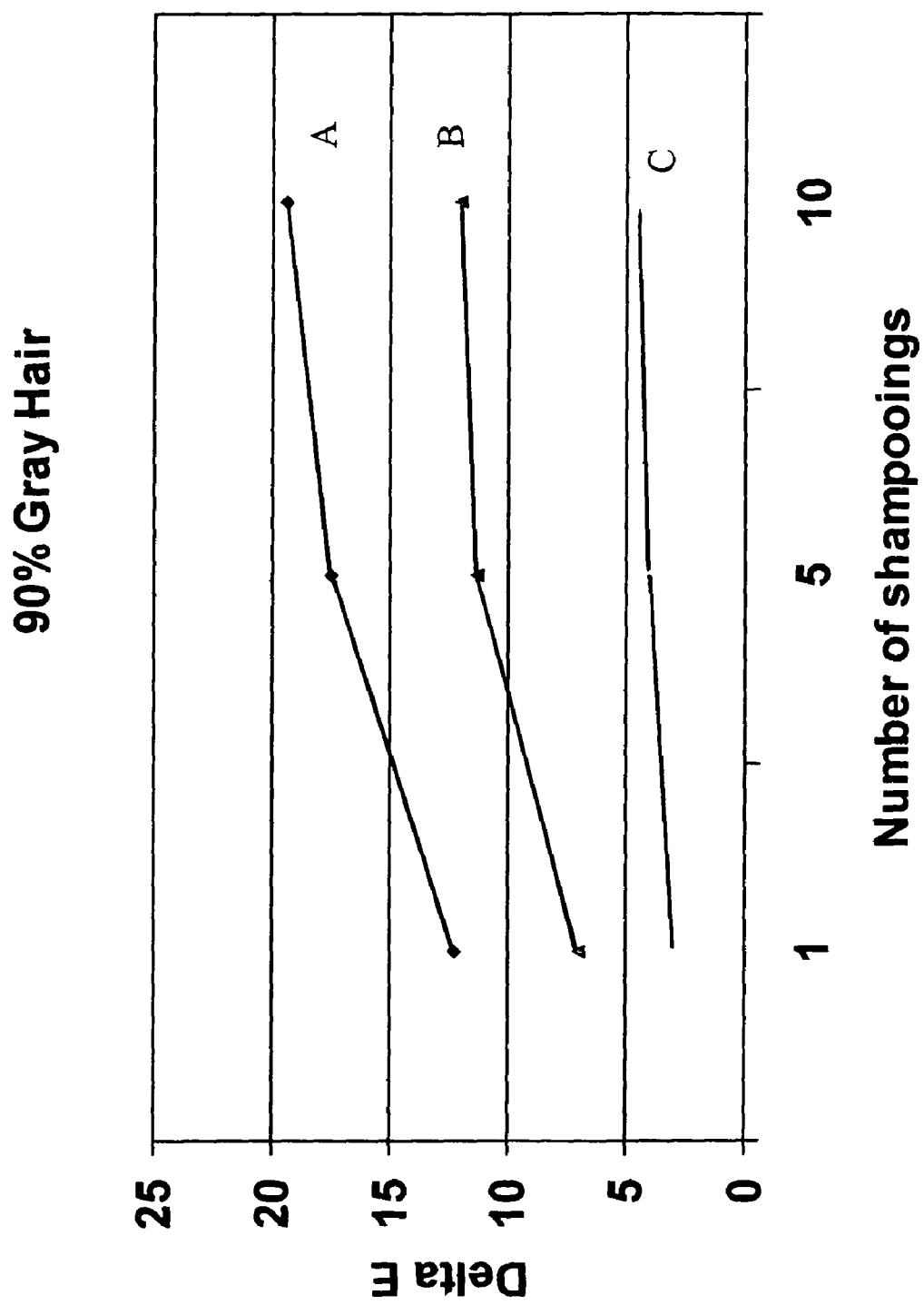
FIG. 1 is a graph of the results of a comparative test of the formulation of Example 1 of the present invention with a formulation of U.S. Pat. No. 7,217,775B2 on gray hair.

The compositions of the invention may be made by dispersing the ingredients in water followed by the application of sufficient heat to dissolve the ingredients without causing decomposition. In the alternative, a suspension may be prepared when one or more of the ingredients are not soluble at the concentrations employed.

All weight percents are based on the total weight of the composition

Example 1 illustrates a typical formulation according to the invention. Sodium lauroyl sarcosinate, lauramidopropyl betaine, cocamidopropylamine oxide and lauramide MEA (N-(2-hydroxyethyl) dodecanamide) are essential to the optimal performance of the invention. Any increase in any of these materials will show a decrease in color take on gray hair. A decrease in these items does not negatively impact the color results, but will decrease the shampoo's ability to produce cosmetically acceptable lather properties. Initial salon testing indicates the concentration of these materials may be lowered by about about 25% while adequate lather will be obtained. The fatty group of each particular surfactant type can be replaced by other similar sized molecules. However, the ones listed have been selected to optimize the lather properties in conjunction with dye take on gray hair. They are currently near the solubility limit of the vehicle and a further increase in concentration will not improve dye take. Lesser amounts can be used to produce other shades.

Suitable fragrances and/or humecants and/or conditioners may also be optionally added to the compositions of the invention as desired. Suitable humecants include di- or polyhydroxy compounds such as glycerin or a liquid form of polyethylene glycol which may be used at a level of 20 to 70 wt %. If high levels of a humecant are used, the amount of water may be reduced. One or more thickeners may be added AT a level of 0.5-1.5 wt %. Typical thickeners include natural gums such as guar gum or a guar gum derivative or a cellulose derivative such as hydroxyethyl cellulose, methyl cellulose, ethyl cellulose or the like. Stabilizers such as chelating agents derived from ethylene diamin tetraacetic acid and/or preservatives such methyl and/or propyl parabens may be added to the formulations of the invention at a level of 0.25-1 wt %. Opacifiers such as a talc, mica or mixtures thereof may be added at a level of 2-4 wt %. Conditioners such as quaternary ammonium compounds which are exemplified by quaternium 91 and the like may be added at a level of 0.5-4 wt %.

Example 1

| Ingredient | Function | Weight % |
| --- | --- | --- |
| D.I. Water | Solvent | 56.170 |
| Quaternized Hydroxypropyl Guar | Thickener/Conditioner | 0.750 |
| Sodium Lauroyl Sarcosinate (30% active) | Surfactant | 10.000 |
| Lauramidopropyl Betaine (30% active) | Surfactant | 10.000 |
| Cocamidopropylamine Oxide (30% active) | Surfactant | 6.000 |
| Lauramide MEA | Surfactant | 6.200 |
| Hydroxyethylcellulose | Thickener | 0.750 |
| Disodium EDTA | Chelating Agent | 0.100 |
| Sodium Citrate | pH buffer | 0.100 |
| Caramel | Cosmetic colorant | 2.000 |
| Basic Blue 99 | Hair dye | 0.491 |
| Basic Brown 17 | Hair dye | 0.207 |
| Basic Brown 16 | Hair dye | 0.466 |
| Basic Red 76 | Hair dye | 0.008 |
| Basic Yellow 57 | Hair dye | 0.008 |
| Mica/Titanium Dioxide | Opacifier | 3.000 |
| Propylene Glycol (56%), Diazolidinyl Urea (30%), Methylparaben (11%), & Propyl paraben (3%) | Preservative | 1.000 |
| Fragrance | Fragrance | 0.750 |
| Quaternium 91 (40%), Cetrimonium Methosulfate (27.5%), & Cetearyl Alcohol (32.5%) | Conditioner | 2.000 |

Procedure:
1) To the batch vessel, add the D.I. Water and disperse the Guar and Cellulose gums with a propeller mixer.
2) Begin heating the batch to 70-75° C. and add disodium EDTA and sodium citrate. Mix until dissolution is complete.
3) Add the surfactants and Quaternium 91 conditioning mixture with mixing. Mix until a uniform solution is apparent.
4) Add the dyes and mica/titanium dioxide material while maintaining the temperature. Mix for 30 minutes.
5) Cool the batch to 50-55° C. and add the caramel and the preservative composition.
6) Cool the batch to 40-45° C. and add the fragrance. Mix until uniform.

The shampoo of Example 1 was compared to two other shampoos that impart color to hair as described in published patents. In both instances the vehicles were made up exactly as disclosed in the patents, and the dyes were replaced with the Basic Dyes as used in Example 1. All three formulas were then dyed out on 90% gray hair and pure white hair as supplied from International Hair Importers. The dye out procedure simply involves 2 lathers of the shampoo with rinsing; followed by blow drying of the swatches. The procedure was repeated over a 10 day period, allowing for a typical build-up period of the color on hair. The color was measured at the 1, 5, and 10 application points using a Minolta 508d Spectrophotometer and the Hunter L,a,b scale. The change in total color (delta E) is the best method to demonstrate color take on swatches as compared to the original untreated hair. Delta E is calculated as follows: delta E=square root of (delta $L^2$+delta $a^2$+delta $b^2$). When the data is graphed, greater color take can be easily seen as higher points on the plot. A difference of 0.5-1.0 is visually detectable. In the case of the formulation of Example 1, the delta E's of 5 to 13 are substantially beyond either comparative patent example sited. The present invention illustrates a significant improvement in the results obtainable using the prior art formulations in this field. This improvement is surprising and unexpected because in the absence of the claimed surfactant package in a shampoo dye, different results are obtained.

Comparative Example A

Example 7

Color Shampoo from U.S. Pat. No. 7,217,752 B2

| Ingredient | Weight % |
| --- | --- |
| D.I. Water | 67.140 |
| Acrylates Crosspolymer (100%) | 3.000 |
| Disodium EDTA | 0.050 |
| Butylene Glycol | 5.000 |
| Sodium Cocoamphoacetate (39%) | 14.230 |
| Cocamidopropyl Betaine (30%) | 3.500 |
| Polyquaternium-39 | 0.800 |
| Germaben II (propylene glycol, diazolidinyl urea, methylparaben, and propylparaben) | 0.450 |
| Sodium Hydroxide (18%) | 0.250 |
| Dimethicone copolyol | 0.200 |
| Decyl Glucoside (50%) | 4.000 |
| Mica/Titanium Dioxide | 0.200 |
| Basic Blue 99 | 0.491 |
| Basic Brown 17 | 0.207 |
| Basic Brown 16 | 0.466 |
| Basic Red 76 | 0.008 |
| Basic Yellow 57 | 0.008 |

Comparative Example B

Example 3

Color Refresher Shampoo from U.S. 2007/0017039 A1

| Ingredient | Weight % |
| --- | --- |
| D.I. Water | 77.720 |
| Sodium Laureth Sulfate | 10.000 |
| PEG-3 Distearate | 2.000 |
| Cocoamidopropyl Betaine | 4.000 |
| PEG-200 Hydrogenated Glyceryl Palmate | 1.000 |
| SD 40 Alcohol | 2.000 |
| Sodium Chloride | 1.000 |

-continued

| Ingredient | Weight % |
| --- | --- |
| Phenoxyethanol | 0.500 |
| Methylparaben | 0.200 |
| Propylparaben | 0.100 |
| Fragrance | 0.300 |
| Basic Blue 99 | 0.491 |
| Basic Brown 17 | 0.207 |
| Basic Brown 16 | 0.466 |
| Basic Red 76 | 0.008 |
| Basic Yellow 57 | 0.008 |

Change in total color from untreated swatches (delta E) for 90% Gray Hair (FIG. 1)

| Sample | 1 Treatment | 5 Treatments | 10 Treatments |
| --- | --- | --- | --- |
| Shampoo, Example 1 (A) | 12.2 | 17.5 | 19.4 |
| Comparative Example A, U.S. Pat. No. 7,217,752 B2 (B) | 3.0 | 4.0 | 4.5 |
| Comparative Example B, U.S.2007/0017039 A1 (C) | 7.0 | 11.3 | 12.0 |

Change in total color from untreated swatches (delta E) for Pure White Hair (FIG. 2)

| Sample | 1 Treatment | 5 Treatments | 10 Treatments |
| --- | --- | --- | --- |
| Shampoo, Example 1 (A) | 19.0 | 26.4 | 29.1 |
| Comparative Example A U.S. Pat. No. 7,217,752 B2 (B) | 5.9 | 6.0 | 8.2 |
| Comparative Example B, U.S.2007/0017039 A1 (C) | 6.7 | 15.4 | 16.2 |

The invention claimed is:

1. A shampoo coloring formulation for human hair which comprises;
   (a) cationic dye;
   (b) sodium lauroyl sarcosinate;
   (c) lauramidopropyl betaine;
   (d) cocamido propylamine oxide;
   (e) N-(2-hydroxyethyl)dodecanamide (Lauramide MEA) and
   (f) water.

2. A shampoo coloring formulation for human hair as defined in claim 1 which comprises;
   (a) from 0.5-2 wt % cationic dye;
   (b) from 5-15 wt % sodium lauroyl sarcosinate
   (c) from 5-15 wt % lauramidopropyl betaine
   (d) from 2.4-10 wt % cocamido propylamine oxide
   (e) from 2.5-10 wt % N-(2-hydroxyethyl)dodecanamide (Lauramide MEA); and
   (f) from 40-65 wt % water.

3. A shampoo coloring formulation for human hair as defined in claim 2 which includes a thickener.

4. A shampoo coloring formulation for human hair as defined in claim 3 which includes a stabilizer.

5. A shampoo coloring formulation for human hair as defined in claim 4 which includes an opacifier.

6. A shampoo coloring formulation for human hair as defined in claim 5 which includes an chelating agent.

7. A method of dyeing human hair which comprises shampooing the hair with a formulation of claim 1.

8. A method of dyeing human hair which comprises shampooing the hair with a formulation of claim 2.

9. A method of dyeing human hair which comprises shampooing the hair with a formulation of claim 3.

10. A method of dyeing human hair which comprises shampooing the hair with a formulation of claim 4.

11. A method of dyeing human hair which comprises shampooing the hair with a formulation of claim 5.

12. A method of dyeing human hair which comprises shampooing the hair with a formulation of claim 6.

\* \* \* \* \*